United States Patent [19]

Brockington

[11] 4,392,873

[45] Jul. 12, 1983

[54] CONTINUOUS VAPOR PHASE CHROMATOGRAPHY

[76] Inventor: Francis R. Brockington, 4016 MacGregor Dr., Columbia, S.C. 29206

[21] Appl. No.: 272,964

[22] Filed: Jun. 12, 1981

[51] Int. Cl.$^3$ .............................................. B01D 15/08
[52] U.S. Cl. .......................................... 55/67; 55/77; 55/197; 55/386; 55/390
[58] Field of Search ................. 55/28, 67, 77, 78, 197, 55/351, 386, 390; 210/657, 198.2

[56] References Cited

U.S. PATENT DOCUMENTS

| | | | |
|---|---|---|---|
| 2,539,006 | 1/1951 | Berg ..................................... | 183/4.2 |
| 2,743,818 | 5/1956 | Higochi ............................. | 55/386 X |
| 2,893,955 | 7/1959 | Coggeshall ........................ | 55/67 X |
| 3,016,107 | 1/1962 | Strange et al. .................... | 55/386 X |
| 3,057,183 | 10/1962 | De Ford ............................ | 55/386 X |
| 3,338,031 | 8/1967 | Barker et al. ............................ | 55/67 |
| 3,369,874 | 2/1968 | Wilhelm .............................. | 55/67 X |
| 3,684,705 | 8/1972 | Matsumoto ....................... | 210/198.2 |
| 4,042,350 | 8/1977 | Phillips ............................... | 55/67 X |
| 4,204,952 | 5/1980 | Snyder ................................. | 210/31 |
| 4,302,222 | 11/1981 | Miller et al. ....................... | 55/390 X |

OTHER PUBLICATIONS

P. E. Barker and S. Al-Madfai, J. Chromatographic Science, 7, 425, (1969).
V. H. Pichler and H. Schulz, Brennstoff-Chemie, Nr. 9/10 Bd. 39, 148 (1958).
P. E. Barker and D. Critcher, Chem. Engng. Sci., 13, 82 (1960).
G. R. Fitch, M. E. Probert and P. F. Tiley, J. Chem. Soc., 4875 (1962).

Primary Examiner—John Adee

[57] ABSTRACT

A method of continuously separating a mixture into its various components using vapor phase chromatography in which both the liquid/solid phase and the fluid (gas) phase are mobile.

6 Claims, No Drawings

CONTINUOUS VAPOR PHASE CHROMATOGRAPHY

FIELD OF THE INVENTION

The present invention relates to a chromatographic method and process in which both the fluid (gas) phase and the liquid/solid phase are mobile and are moving counter currently through a thermal gradient.

BACKGROUND OF THE INVENTION

The utility of a continuous separation process such as fractional distillation has been recognized for over 30 years. In 1951 C. H. O. Berg described in U.S. Pat. No. 2,539,006 a process whereby gases could be selectively adsorbed onto a solid adsorbent (activated charcoal) in a continuous manner. In this process the adsorbent passed successively through zones of stripping, adsorption, heating, sealing, selective desorption and back to stripping resulting in an effluent gas stream enriched in one or more of the desired components. The apparatus was designed principally for purifying a low molecular weight (less than $C_5$'s) organic gas stream.

The concept of using a moving bed or a mobile liquid/solid phase counter currently to the flow of the vapor phase in gas liquid chromatography to continuously separate two components was introduced by V. H. Pichler and H. Schulz in an article in Breenstoff-Chemie, Nr. 9/10 Bd. 39, 148 in 1958 and later followed up by P. E. Barker and D. Critsher, Chem. Engng. Sci., 13, 82 (1960) and G. R. Fitch, M. E. Probert and P. F. Tiley, J. Chem. Soc., 4875 (1962). They found in their experiments that a gas stream saturated with at least two components, entering an isothermal column containing a mobile bed moving counter current to the gas stream would under certain conditions elute one of the components with the gas phase while the other component or components, having a greater affinity for the liquid phase, would be retained and ultimately carried to a region where it would be stripped off.

In 1969, P. E. Barker and S. Al-Madfai with the help of Universal Fisher Engineering Company, Crawley, England designed and built a continuous chromatograph employing the principles outlined in the preceding paragraph. The continuous chromatograph was used to purify cyclopentane and cyclohexane; J. Chromatographic Science, 7, 425 (1969).

The major advantage of a continuous chromatography system lies in the prospect that respectable throughputs can be achieved without sacrificing the powerful separating capability of conventional chromatography. L. R. Synder, U.S. Pat. No. 4,204,952 May 27, 1980 using tandem chromatographs and seriatim sample injections has attempted to optimize throughput by taking slices from one chromatogram to be used as an input for the second chromatogram; thereby reducing the overall time for any single chromatogram.

SUMMARY OF THE INVENTION

The physical processes of chromatography, specifically vapor phase chromatography (VPC) have been thoroughly chronologued, and are well known to those familiar with the art. In conventional VPC there is a stationary liquid/solid phase and a mobile gas phase, and the relative differential interaction of the components of the mixture with these two phases culminates in the desired separation. The number of interactions, a quantitative intergerized reflection of the degree of separation, is sometimes reported in number of theoretical plates, in analogy to distillation.

Continuous chromatography utilizes the same elements of conventional chromatography, differing only in that all processes are dynamic. The conventionally stationary liquid/solid phase is mobile and moving in direction opposite the gas phase and through an increasing temperature gradient. Continuous chromatograhy, like continuous fractionalization, has the potential of achieving relatively large material throughput, unlike conventional chromatography which is a discrete process, while still retaining most of the powerful separation characteristics inherent with chromatography.

The single most distinctive element of the instant invention is that both phases are mobile and moving in opposite directions through a temperature gradient. One phase is solid, being comprised of typical chromatography materials or a flexible porous polymer. The solid phase may be coated with a liquid of low volatility as is commonly utilized in gas liquid chromatography. Hence in continuous chromatography the liquid/solid phase which conventionally is stationary, is mobilized. The gas phase as in conventional VPC is also mobile and is comprised of gases typically common to the art. The chromatography column has a thermal gradient impressed upon it and is fitted with at least two intersecting ducts through which fractional proportions of the carrier gas can exhaust. The gradient is formed by utilizing heat exchangers maintained at incrementally higher temperatures and positioned along a well insulated column. The gradient slope is dependent on the distance between the exchangers and their respective temperatures. The column and heat exchangers must have adequate heat transfer properties such that the exchangers can deliver and remove heat at a rate sufficient to maintain the desired thermal gradient. The collection ducts which are dispersed along the length of the column between the entrance (cold end) and the exit (hot end) are usually fitted with a high volumn condenser and flow control value. Fractional proportions of the carrier gas are continuously split off from the main stream of the column, and the less volatile components of the sample are condensed out of the split stream. The liquid/solid phase moves from entrance to exit, and the fluid (gas) phase moves from the exit to the entrance. The mixture to be fractionated is fed as a liquid or hot gas at the cool end or entrance of the column and is transported by the liquid/solid phase toward the exit. As the components of the mixture are carried toward ever increasing temperatures they will have disproportionate affinities for the gas phase which is moving in the opposing direction. Just as in convention VPC, bands of the individual components form; dispersed along the length and breadth of the column. Unlike conventional VPC in which these bands eventually elute in a serial fashion, in continuous chromatography a steady state will be reached between the two phases, and the bands will essentially be stationary, located near a collection duct from whence they can be collected. The components which exhibit a greater affinity from the gas phase will be located nearer the column entrance than those components having a relatively lesser affinity. By varying the slope of the thermal gradient, or the rate of flow of the liquid/solid phase or the gas phase, the bands can be moved to different sites along the column. The process of establishing the optimum column conditions will be largely one of experience and trial and error.

DETAILED DESCRIPTION OF THE INVENTION

The chromatography column is constructed of metal, glass and/or ceramic materials. In general stainless steel is the material of choice in light of its inertness, wear resistance, strength and thermal properties. Aluminium or copper cladding can be added to ensure good heat transfer. This is especially preferable at sites of heat exchangers such as at the exit and entrance. The column exchangers can be heated via electrical heating elements, steam, and/or oils such as Dow-Therm ® (Dow Chemical Co.), silicone oils, mineral oils, polyols, ethylene glycol, et cetera. The column heat exchangers can be cooled by utilizing conventional coolants such as forced air, water, ethylene glycol and Freons ® (Dupont), but if necessary liquid nitrogen or other cryogenic fluids can be employed. In a typical application employing only two heat exchangers, one transferring heat to the column, the other removing heat, the exchangers are each 1½ feet long sections of copper jacketing enclosing the column and separated from each other by a distance of seven feet. Cool water circulates through one and steam through the other.

In a slightly more complex system involving a longer column there might be multiple heat exchangers, and the temperature in each would be controlled as determined for the particular chromatogram. This would give the operator the versatility of programming chromatograms with different temperature gradients.

The diameter of the column will be end use dependent, but a practical range is ¼ inches to 6 inches. The preferred morphology of the column is circular although alternative shapes, (i. e. oval, rectangular) are not excluded, and as Example 1 will demonstrate are in certain cases preferred. The length of the column is insulated with traditional materials such as asbestos, fiberglass, clays, mineral salts and other well known insulating materials. Depending on the upper temperature limit of the design of the column, plastics such as epoxies, phenolics, malamines and foams such as polyurethane, polystyrene and silicone can also be employed. There are multiple commercial laminates available which are suitable and easily applied such as Thermazip ® by Accessible Products Company.

Positioned along the column are a series of collection ducts, which are smaller in diameter than the chromatography column. The ducts tap into the column and exhaust preferably through a high volumn condenser (i. e. Friedricks, Graham, Hopkins) and a flow control valve. The rate of exhaust being a fraction of the carrier gas flow rate.

The column can have as many ducts as the intended end use dictates, however, a reasonably practical number is between 3 and 100 with 20 being a good compromise between throughput, resolution, versatility and cost. The ducts like the column are preferably well insulated. Unless the ducts are constructed of extremely poor conductors such as boron silicate glass, supplemental heating is to be avoided as it tends to disrupt the column's gradient.

The mobile liquid/solid phase is conveyed through the column in any convenient manner such as on a web, as a web, a substrate in any auger type screw conveyer, a substrate in a porous inner tube moving convergent within the column or as a porous cellular substrate shaped into a rod.

The web can be constructed of any material suitable for matting, weaving, twisting, braiding, knitting or otherwise fastened such as cotton, glass, polyester, paper, asbestos, polyacrylic, ceramic fibers, et cetera; and it may be reinforced with a matrix or beams of materials having high tensile moduli. The web may be coated or impregnated with a liquid commonly used in gas liquid chromatography such as polyethers, silicones, polyesters, polyglycols, aliphatic hydrocarbons and polyamides.

In conventional gas chromatography the column is packed with a solid substrate which is either granular or bead in form and composed of diatomite, sand, Teflon ® (Dupont), inorganic salts, glass, carbon black or activated carbon. In the instant invention these substances can be mobilized either in an auger screw type conveyor or as a porous tube moving through the column. The solid phase can be treated with liquids commonly used in gas liquid chromatography such as those recited in the previous paragraph and are common to those skilled in the art.

The auger screw can be constructed of any suitable metal or glass such as steel and alloys thereof, or boron silicate glass. In the case of a stainless steel column the preferred composition of the screw is stainless steel. The inside of the column can be lined with silicone or neoprene rubber or Teflon ® to reduce wear.

The mobile porous tube should allow for the ready free flow of gases through its walls while being fine enough in mesh to retain the solid phase. The walls should be as thin as possible while still retaining the integrity of its morphology. Braided metal, fiberglass and ceramic fibers are the preferred materials of construction. The outside diameter of the tube should be just slightly smaller than the inside diameter of the column thus allowing for relatively easy movement through the column.

When utilizing a porous cellular substrate shaped into a rod, the rod acts as the conveyor and the solid phase. In general only very light coatings (1% or less) of the conventional chromatographic liquids will be applicable, and therefore, consideration must be given to choosing the correct porous substrate for the end use application. In general only modest temperatures (300° F.) will be practical with this technique. Typical of such materials are porous polyethylene, polypropylene, polyvinyl fluorides, polyurethane, silicones and polyamides. Gases must pass freely through the substrate in all directions, and a lower practical limit on the pore size is around 150 microns. The rod which must nearly conform with the morphology of the column can be reinforced with a flexible endoskeleton such as a colinear wire or steel mesh.

In continuous chromatography the liquid/solid phase using a variable speed driven screw or pulley is cycled back to the entrance after exiting the column; circulating against a gas stream moving in the counter direction. The carrier gas must move through the liquid/solid phase, and therefore, must be of sufficient pressure to overcome the combined static and dynamic effects of the pressure drop over the liquid/solid phase. The necessary carrier gas pressure at the exit of the column can be maintained through the utilization of a number of techniques. In the case of the web a simple squeeze roll will effect sufficient back pressure. The auger uses a series of pressurized chambers in a manner analogous to locks. The porous tube and porous rod can be fitted with unidirectional pressure valves or as one of the examples illustrate, half of the column can be used for chromatography while the other half serves simply as a vehicle to build the back pressure.

The mixture to be fractionated is introduced at a metered rate to the column as a vaporized hot gas or dripped or sprayed directly onto the liquid/solid phase. With use of the auger, solids can be added directly in conjunction with the substrate.

In optimizing the column conditions for the collection of the desired components of a mixture, the variables (column length, temperature, phase composition, flow rates) common to both continuous and conventional chromatography are the tools of enhancing resolution, and are familiar to those skilled in the art. Ideally the operator balances these factors until a satisfactory compromise between purity and output is achieved.

The operating parameters of the instant invention are by nature of the invention flexible, but a guide for recommended starting points are as follows:

| Fluid (gas) flow rate | 10–40 | $cm^3$/min/100 $mm^2$ |
| Liquid/solid flow rate | 5–25 | $cm^3$/min/100 $mm^2$ |
| Sample feed rate | 20–200 | ug/min/100 $mm^2$ |

The sum total of the duct flow is in most cases not greater than 10% of the fluid (gas) flow, where 100 $mm^2$ is the cross-sectional surface area of the column.

The fluid (gas) phase can be comprised of but not limited to fluids commonly utilized in gas chromatography such as nitrogen, argon, neon, helium, air, hydrogen, carbon dioxide, inerted air or less traditional fluids such as low molecular weight hydrocarbons and their halogen, sulfur and oxygen derivatives such as methane, difluorodichloromethane, carbon disulfide and methanol.

As the method of choice by which the liquid/solid phase will be mobilized is essential to the practice of the invention, five methods have been cited as examples. The examples are not meant to be restrictive, as there are multiple physical mechanical combinations and permutations by which the invention can be practiced, but as illustrative best mode embodiments for specific end use applications.

EXAMPLE 1

The column in a linear oval, 20 feet long, having a diameter at its widest point of 2 inches and ¼ inches at its narrowest. It is constructed of stainless steel, and is insulated with multiple layers of asbestos. The last 2 feet of the exit end are heated with a circumventing steam (40 psi) jacket, and the first 3 feet of the entrance are cooled with circulating cool water. There are three ducts, also constructed of stainless steel, ⅜ inches in diameter, located every 5 feet along the column each of which is fitted with a condenser and a flow control valve. A coarse open mesh fiberglass cloth belt, 2 inches wide and 3/16 inches thick, circulates through the column and around back to the entrance over a series of rollers, at least one of which is driven by a variable speed drive. The column is preferably mounted vertically. Two rubber rollers are flush mounted against the exit of the column and gently squeeze the web.

The gas carrier inlet is fitted with a flow control valve, and the inlet is mounted just prior to the exit. The carrier gas or gas phase is dry, inerted air. The fiberglass web is coated with a 5% w/w methyl silicone coating such as SP 2100 ®, a trade name of Supelco. The mixture to be fractionated is evenly applied as a liquid to the web at a metered rate just prior to the column entrance through the use of a variable speed gear pump (or any other system which is not pulsed). The gas exhaust flow rate at the entrance of the column is approximately 900 ml/min and 33 ml/min at each of the three ducts. The web moves at approximately 4"/min. The continuous chromatography unit is designed for separating relatively simple mixtures, such as ethanol and water, which because they form an azeotrope can not be separated entirely using standard distillation techniques.

EXAMPLE 2

The column is a stainless steel cylinder 40 feet long and 5 inches in diameter. The interior walls of the column are coated with a silicone rubber having a high load of a good thermal conductor. An auger runs through the center of the column, and it is so constructed that its threads are nearly convergent with the walls of the column. The center rod of the auger is hollow, having an interior diameter of 1¾ inches. There are fourteen ducts, each with a condenser and an air flow valve. The ducts are mounted on the column at a spacing of one every 2 feet 8 inches, have a ⅜ inch diameter, and are constructed of stainless steel. An 80 mesh screen covered eyelet is mounted in each of the ducts at its site of attachment to the column. The column is fitted with four heat exchangers, the mid-points of which are located every 10 feet. The exchangers are formed by coiling ¼ inch diameter copper tubing around the column, and then soldering the coil to the column. The coil length is approximately 2 feet and is situated between ducts. The hollow center of the auger rod is also fitted with four heat exchangers, and they are positioned opposite the column exchangers. The two end exchangers are formed similar to the column heat exchangers using smaller diameter tubing, while the two interior units, located at 20 and 30 feet, are baffled copper cylinders (1¾"×3') flush mounted in the hollow rod. The exchangers fluid medium is fed from the entrance and the exit of the column to the cylinders at 20 feet and 30 feet respectively, through insulated annualated tubes which are centered in the hollow rod. The outside diameter of the effluent tube being about 1 inch, and the feed tube within it being approximately 0.7 inches in diameter. The tube insulation is aluminium boron silicate fiber packing. The entire length of the column is also insulated with the same material. The exchanging medium is ethylene glycol for all four pairs of heat exchangers.

The column is tilted upwards at a 30° angle. The auger is driven by an AC motor coupled through a variable speed gear box. Just past the heat exchanger at the column entrance there is a 3 inch diameter opening cut into the column which vents to a shallow hopper which feeds the liquid/solid phase to the column, (glass beads with a 1% silicone coating). The mixture to be separated is sprayed through an airless sprayer at a metered rate onto the beads.

The beads pour out the column exit through an elbow connected to a (3'×5") glass pipe vertically mounted and fitted with two ball valves 3 feet apart. The section between the column and the first valve (chamber 1) and the 3 foot section between the two valves (chamber 2) are both pressurized with the carrier gas, nitrogen. By sequentially operating the valves, the beads can be collected and recycled back to the entrance hopper without disturbing the pressure in chamber 1 or the column. The flow rate of the carrier gas through the column is approximately 3 liters/min, and the duct flow rate is 50 cc/min. The liquid/solid phase is pushed through the column at 1 liter/min.

EXAMPLE 3

The column is cylindrical, 2½ inches in diameter and 80 feet long, constructed of stainless steel, having a U shape configuration, and is mounted vertically such that the loop of the U is on the bottom. Only half of the column, or one leg and half of the loop (designated the right leg) are utilized for chromatographic purposes, with the other half of the column serving only as a device for building back pressure. There are 20 ducts located on the right leg or about one every 23 inches. Each duct except the first which is ½ inch in diameter is ¼ inch in diameter and is fitted with a condenser and a flow control valve. The carrier gas, nitrogen, enters the column at the center of the loop of the U through a ½ inch tube fitted with a flow control valve.

The right leg of the column has five heat exchangers and a heated sample inlet port. The first exchanger, located at the entrance of the column is a 1½ foot jacket cooled with circulating ethylene glycol at $-20°$ C. The next four exchangers, their mid-points approximately 8 feet apart are 1 foot coiled jacketed units fashioned in a manner as described in Example 2, and have circulating Dow Therm. The temperature of the medium is regulated to the desired temperature for the chromatogram.

The sample inlet port, a $\frac{3}{8}''\times 12''$ Pyrex ® tube electrically heated and stoppered with a septum, intercepts the column just past the low temperature exchanger; approximately 1 foot 7 inches from the entrance. The entire right leg of the column is insulated.

The liquid/solid phase (40 mesh Chromosorb W ®, Applied Science with 5% Carbowax ®, Union Carbide) is transported through the column in a 2⅜ inch diameter sleeve composed of ceramic braided fibers (Nextel ®-312, 3M Co.). The sleeve is connected end to end, and traverses circularly through the column and over a variable speed driven pulley mounted at the top of the U.

The sample mixture is continuously injected at a metered rate through a needle puncturing the injection port septum, where it vaporizes, thereby forcing it out of the port and onto the column where it condenses onto the liquid/solid phase in the vicinity of the cold #1 heat exchanger.

The carrier gas flow rate at the entrance is 10 liters/min and 300 cc/min through each duct except the first duct which has a flow rate of 40 liters/min. The liquid/solid phase flows at 28.5 liters/min. The sample feed rate is 250 mg/min.

EXAMPLE 4

The column configuration is the same as described in Example 3. The liquid/solid phase, however, moves through the column as a continuous element approximately 90 feet in circumference and 2⅜ inches in diameter. The element (or rod as it has been referred to) is composed of porous polypropylene ® (Glasrock Products Inc., Porex Div.) and it has a pore size of 250 microns. The liquid coating is 0.5% SP 2100 ®, Supelco.

EXAMPLE 5

The column configuration and the liquid/solid phase conveyance are the same as described in Example 3 with the following modifications. In the left leg of the U (the back pressure side) 20 feet from the carrier gas entrance there is an inlet tube through which Freon ® (Dupont), is pumped at a metered rate such that after it expands it produces a pressure nearly equal the carrier gas pressure. Ten feet up the left leg of the column from that point there is an exhaust duct which is connected to a compressor with accompanying cooling fins. The compressor collects the Freon from the column and condenses it. Following condensation it is circulated back through the Freon inlet tube onto the column.

What I claim is:

1. A chromatographic process in which both the gas phase and the liquid/solid phase are mobile and traversing in opposing directions through a common column which has one or more thermal gradients impressed lengthwise across it, and in which a mixture to be chromotograph is continuously introduced, partitioned and collected as fractions from the gas phase where:
   A. The said thermal gradients are formed by simultaneously heating a section of the column and cooling another section through the use of heat exchangers;
   B. The said liquid/solid phase moves in direction in the column toward increasing column temperatures;
   C. The said gas phase moves in a direction opposite the liquid/solid phase and toward increasing column temperatures;
   D. The said mixture to be chromatographed is introduced to the column at the lower temperature end of the column and at a metered rate;
   The said fractions of the mixture are collected through the use of ducts which are dispersed along and intersect with the column, and said ducts are fitted with condensers and gas flow control devices.

2. The chromatographic process in claim 1 in which the number, range and slope of the thermal gradients is controlled.

3. The process of claim 1 in which the liquid/solid phase is conveyed through the column as a substrate on a web or as a web.

4. The process of claim 1 in which the liquid/solid phase is conveyed through the column as a substrate by an auger type screw conveyor.

5. The process of claim 1 in which the liquid/solid phase is conveyed through the column as a substrate in a porous, inner tube moving within the column.

6. The process of claim 1 in which the liquid/solid phase is conveyed through the column as a substrate, said substrate itself being formed into a porous, flexible rod.

* * * * *